(12) United States Patent
Millan

(10) Patent No.: US 6,411,776 B1
(45) Date of Patent: Jun. 25, 2002

(54) ELECTRIC HEATING DEVICE WITH EMISSION OF ACTIVE SUBSTANCES

(75) Inventor: Jordi Basagañas Millan, Cerdanyola del Valles (ES)

(73) Assignee: DBK Espana, S.A., Cerdanyola del Valles (ES)

( * ) Notice: Subject to any disclaimer, the term of this patent is extended or adjusted under 35 U.S.C. 154(b) by 0 days.

(21) Appl. No.: 09/446,353
(22) PCT Filed: Jun. 18, 1997
(86) PCT No.: PCT/ES97/00157
§ 371 (c)(1), (2), (4) Date: Apr. 11, 2000
(87) PCT Pub. No.: WO98/57674
PCT Pub. Date: Dec. 23, 1998
(51) Int. Cl.[7] ................................ F24F 6/08; F24F 3/14
(52) U.S. Cl. ...................................... 392/395; 392/390
(58) Field of Search ..................... 392/386, 390, 392/392, 394, 395; 122/366; 261/DIG. 65, 142, 99; 219/541, 544

(56) References Cited

U.S. PATENT DOCUMENTS

| 3,835,434 A | * | 9/1974 | Kahn ........................ 218/544 |
| 4,331,860 A | * | 5/1982 | Roller et al. ............. 388/22 R |
| 4,874,924 A | * | 10/1989 | Yamamoto et al. ......... 392/395 |
| 5,940,577 A | * | 8/1999 | Steinel ...................... 392/395 |

FOREIGN PATENT DOCUMENTS

JP        4167391        * 6/1992

* cited by examiner

*Primary Examiner*—Sang Paik
(74) *Attorney, Agent, or Firm*—Notaro & Michalos P.C.

(57) ABSTRACT

An electric heating device releases active substances and has a housing (1) and cover (3) with holes (2) and (4) to receive a wick that is to be heated and soaked in a liquid that is to be evaporated. The housing (1) receives a pill-shaped PTC element (5) which is pressed between two electrodes (6) and (7) having a high heat conducting coefficient. The device has a small number of parts, and, with electrodes of suitable material and structure, provides a uniform heating of the round body which receives the wick.

5 Claims, 2 Drawing Sheets

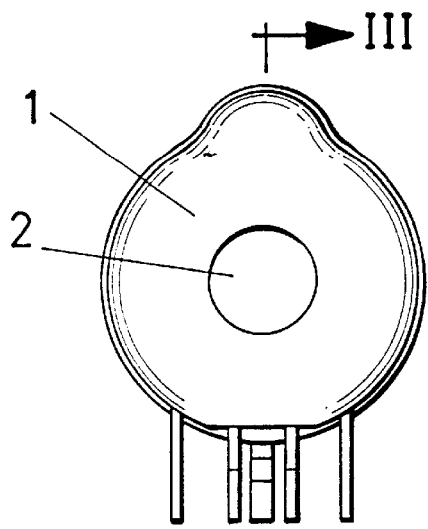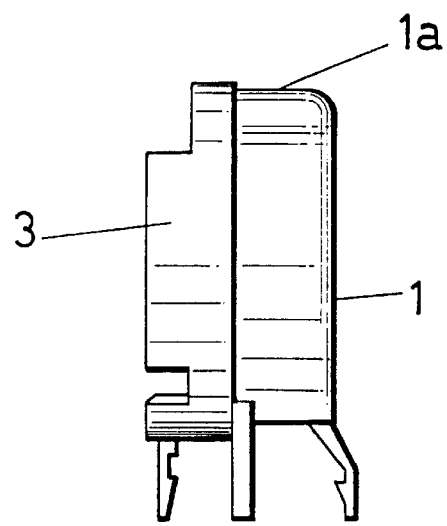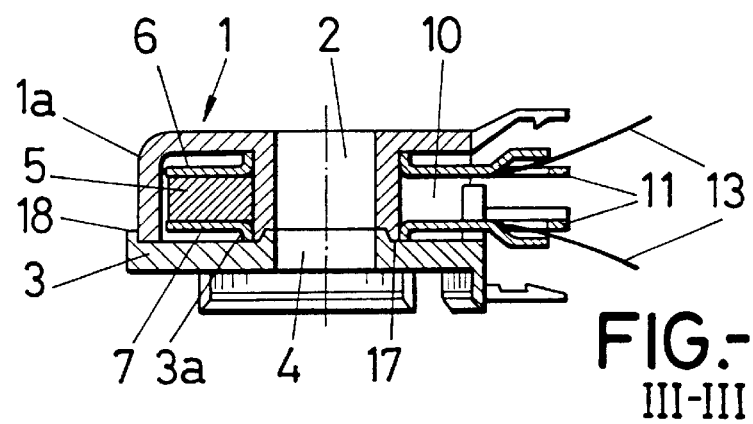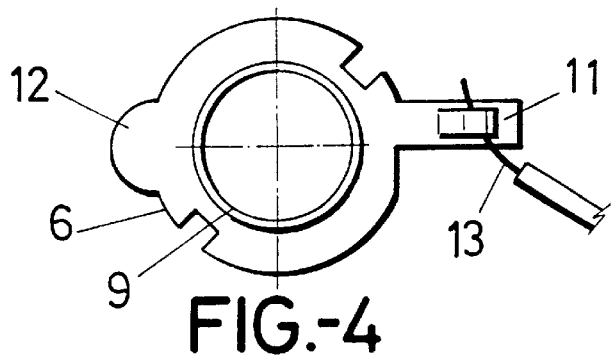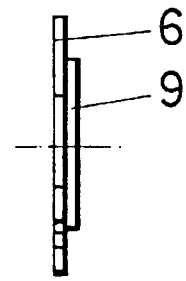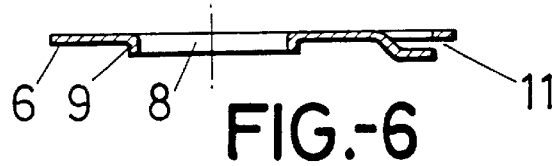

ELECTRIC HEATING DEVICE WITH EMISSION OF ACTIVE SUBSTANCES

The present Patent of Invention relates to a new electric heating device to release active substances that, in addition to the function for which it was designed, affords a number of advantages discussed below and others that are inherent in its organisation and construction.

BACKGROUND OF THE INVENTION

Several state-of-the-art devices exist that are used for evaporating aromatic or active substances, for instance insecticides or fragrances, equipped with electric heating designed to nonpermanently release the active substances, only in case of need.

The aromatic or active substances can thus be supported by solid materials or be liquid.

Several state-of-the-art devices are known, for instance disclosed in registrations such as European Patent 90121288.6, Utility Model no. 9203290/7, Utility Model 9501364/4, and others.

Due to their design, state-of-the-art devices have two drawbacks worthy of note, one of which is the large quantity of constituent parts they have, with the ensuing costs derived from the moulding or manufacturing process of said parts. A second drawback is due to the substantial degree of difficulty the mounting process represents, which poses problems in connection with an automated mounting.

That is why said heating elements are expensive and hence barely competitive as compared with other conventional apparatus designed for similar purposes.

Another drawback of the state of the art is the absence of specific means devised for an easy, optional connection of additional elements, such as timers, adjusters, and others.

SUMMARY OF THE INVENTION

The company applying for the present Patent of Invention has used its expertise in the manufacture of devices of this kind, to devise heating means to heat a body having a round shape, and provided with a hole to receive the wick carrying a means to be evaporated.

A first object of the invention is to achieve an arrangement of the kind aforesaid, designed so as to have a small number of constituent parts, which are sandwiched together in order thereby to provide a fully automatic assembly, which results in substantial costs savings.

A second object of the invention is to provide said device with heating means that use up little electricity in operation and produce a homogeneous heating, irrespective of the supply voltage.

This second object is achieved using a PTC element for the heating to render the quantity of electric power released and the supply voltage independent from each other, due to the peculiar PTC characteristics, which self-stabilise and control temperature within a very wide voltage field.

The invention successfully solves the problem that usually arises when PTC elements are employed, for, being very small components, approximately with a diameter of eight millimetres and a thickness of three millimetres, the transfer of heat energy is locally limited.

Because in the device subject of the invention, the round body, which receives the means to be evaporated, must be heated as uniformly as possible, a special shape and material is used for the electrodes, which are ring-shaped in order to encircle the hole that is to be heated, and made of a material of good heat-conducting characteristics.

This organisation allows a single PTC element to be used to supply power with the ensuing economic savings.

In spite of the power concentration at the PTC location, a very uniform heating is achieved to meet requirements, given the characteristic that the electrodes fully surround the hole that is to be heated.

The improvements in accordance with the present Patent of Invention offer the advantages described hereinbefore and others that will follow easily from the embodiment of a device provided with electric heating having the said improvements that is described hereinafter in further detail for an easier understanding of the characteristics set out above, concurrently referring to a number of details, to which end a number of drawings are attached to the present specification which represent a practical embodiment of the present invention, merely as an example that is not intended to limit the same.

BRIEF DESCRIPTION OF THE DRAWINGS

In the drawings:

FIG. 1 is a top plan view of the device having the improvements subject of the invention.

FIG. 2 is a side elevation view of the device of FIG. 1.

FIG. 3 is a cross-section of the device along III—III.

FIGS. 4, 5 and 6 illustrate the electrode respectively in accordance with plan, side and diametrical cross-section views.

DESCRIPTION OF AN EMBODIMENT OF THE INVENTION

Figure 7:
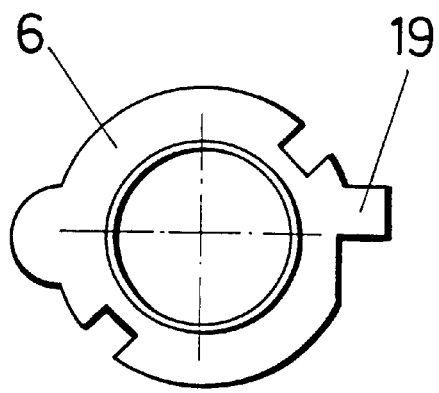
FIG. 7 is a plan view of the electrode, in accordance with an alternative embodiment designed for it to be connected to printed circuit board contacts.
Figure 8:
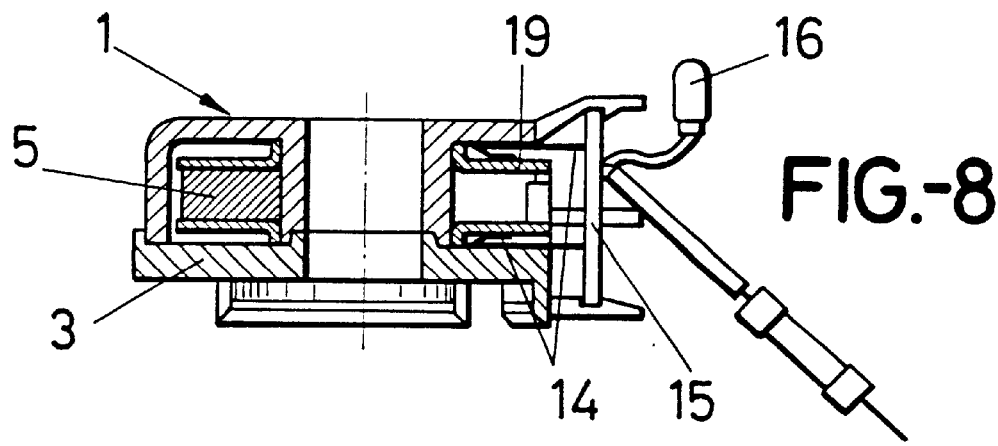
FIG. 8 is a cross-section overview of the device, in accordance with the bulb and printed circuit connection variant.
Figure 9:
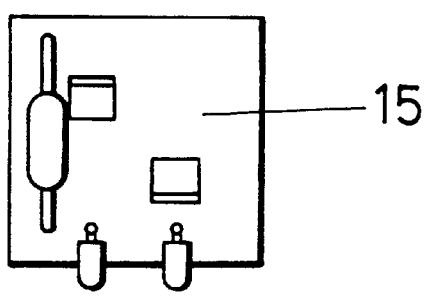
FIGS. 9, 10 and 11 show the printed circuit board respectively in accordance with front, rear and side views.
Figure 10:
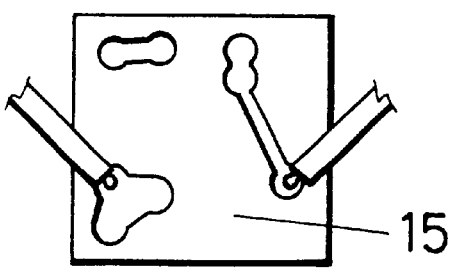
Figure 11:
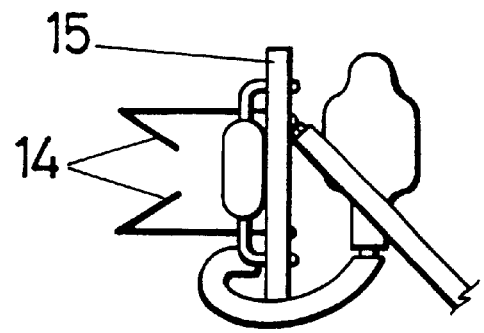

As shown in the drawings, the device equipped with electric heating to release active substances in accordance with the invention and in accordance with an embodiment thereof, comprises a housing made of a moulded plastics material, generally designated -1-, with an axial through hole, -2-.

The housing -1- has a circular shape in plan view, with a perimetric skirt -1a- that is closed with a part -3- that serves as a cover, is similarly circular and has a central hole -4- coinciding with the hole -2-. In order to obtain a lasting closure, the cover -3- and the base of the housing -1- are joined by ultrasonic soldering.

This ultrasonic soldering provides a seal between parts -1- and -3- at areas designated -17- and -18-. The seal -17- serves a safety purpose in order to avoid leakage of electric current towards the wick supporting the substance to be evaporated, which constitutes a conducting element because it is moist. The seal -18- provides a watertight seal to insulate the components located within the housing -1-3-.

The holes -2- and -4- of the housing -1- and cover -3- establish an axial passage into the unit to receive a wick that is to be heated, not shown, soaked in a liquid that is to be evaporated.

A pill-shaped PTC element, designated -5- is located within the unit formed by the housing -1- and cover -3-. This element -5- is mounted between two twin contacts, designated -6- and -7-, made of a material with good heat conduction characteristics shaped as an annulus, as shown in FIGS. 4, 5 and 6. The central hole -8- of said contacts has a diameter equivalent to the wall of the through hole -2-4-, thereby encircling said wall throughout the circumference, in order to provide a homogeneous heat distribution. The said contacts -6- and -7- have an edge -9- around the central hole -8- to offer a greater interface with the wall of the through hole -2- and -4-, thereby improving the heat performance.

In order to prevent the contacts from touching one another at the point diametrically opposite the PTC element, causing a short circuit, supports -10- are provided inside the base to hold the distance given by the thickness of the PTC element between the contacts -6- and -7-.

In order to ensure the required pressure between the contacts -6- and -7- and the PTC element -5-, three coil-like elements -3a- are provided integral with the cover -3-. These elements -3a- are pressed against the top contact, transmitting a biasing force throughout the unit. The contacts -6- and -7- have a tab -11- on the side opposite the extension -12-, for locating the PTC element, which tab serves to connect the conducting wire -13-. This wire -13- is inserted under the tab, as shown in FIG. 4, which is then folded over the wire, thereby ensuring a bond between both components.

If contact is made through a printed circuit board -15-, connection is made through spear-shaped terminals -14- which are snapped into the space left between the electrodes -6- and -7-, and the housing -1- and cover -3-, respectively, making contact with the tab -19- of the relevant electrode, which tab is shorter in this case, as illustrated in FIG. 7.

The printed circuit -15- optionally allows the inclusion of sundry electric devices, namely for instance a timer, adjuster, etc.

In accordance with the description, an arrangement is obtained that works using up very little electricity to produce a homogeneous heating, irrespective of the supply voltage.

The arrangement is convenient in that it comprises only five parts which are sandwiched together, thus allowing an automatic mounting and at the same time an enhanced safety of the element at issue, concurrently resulting in substantial cost savings.

In accordance with the above, in said mounting the PTC element -5- is located between the two contacts -6- and -7- such that the contacts and the PTC element take up a position parallel to the cover -3- and the inner surface of part -1-

The Invention can, observing its essence, be otherwise embodied in practice, with details differing from the embodiment set out as an illustration in the description, and which shall also be covered by the protection applied for herein. It can therefore be constructed in any form and size, with the most suitable materials, since lying within the spirit of the claims.

What is claimed is:

1. An electric heating device to evaporate an active substance, comprising:
   a housing with an electric heating element and adapted for use in an apparatus having a container carrying the substance to be evaporated and a wick through which the substance rises by capillary action up to the electric heating element;
   the housing only comprising two molded parts assembled to each other to make up a closed compact package, a first of the parts making up the housing being circular in plan view with a perimetric skirt covered by a second of the parts serving as a cover, both of said parts having axial through holes and which establish an axial passage to house a wick to be heated which is soaked in the substance to be evaporated, said parts together form an annular enclosure housing a disc-shaped PTC element; and
   two twin electric contacts made of a material hating good heat conduction characteristics and pressed on opposite sides of the PTC element, the contacts being shaped as an annulus and tightly encircling an outer wall of the axial passage consisting of holes and, in order to provide a homogeneous heat distribution, said twin contacts including an axial, perimetric wall for providing a greater contact surface with the outer wall of the axial passage, wherein the first:part of the housing comprises supports positioned diametrically opposite from the PTC element in order to maintain a distance between the contacts, the distance being equivalent to a thickness of the PTC element.

2. An electric heating device to evaporate an active substance, comprising:
   a housing with an electric heating element and adapted for use in an apparatus having a container carrying the substance to be evaporated and a wick through which the substance rises by capillary action up to the electric heating element;
   the housing only comprising two molded parts assembled to each other to make up a closed compact package, a first of the parts making up the housing being circular in plan view with a perimetric skirt covered by a second of the parts serving as a cover, both of said parts having axial through holes and which establish an axial passage to house a wick to be heated which is soaked in the substance to be evaporated, said parts together form an annular enclosure housing a disc-shaped PTC element; and
   two twin electric contacts made of a material having good heat conduction characteristics and pressed on opposite sides of the PTC element, the contacts being shaped as an annulus and tightly encircling an outer wall of the axial passage consisting of holes and, in order to provide a homogeneous heat distribution, said twin contacts including an axial, perimetric wall for providing a greater contact surface with the outer wall of the axial passage, the twin contacts further including respective extensions, the dimensions of which extensions are comprised within limits of a structure made up of the housing and cover, spaces being formed respectively between said housing and cover and said extensions, the extensions being adapted to receive hook-shaped electric connection terminals coupled by elastic pressure in the spaces.

3. An electric heating device to evaporate an active substance, consisting of:
   a housing with an electric heating element and adapted for use in an apparatus having a container carrying the substance to be evaporated and a wick through which the substance rises by capillary action up to the electric heating element;

the housing only comprising two molded parts assembled to each other to make up a closed compact package, a first of the parts making up the housing being circular in plan view with a perimetric skirt covered by a second of the parts serving as a cover, both of said parts having axial through holes and which establish an axial passage to house a wick to be heated which is soaked in the substance to be evaporated, said parts together form an annular enclosure housing a disc-shaped PTC element; and two twin electric contacts made of a material having good heat conduction characteristics and pressed on opposite sides of the PTC element, the contacts being shaped as an annulus and tightly encircling an outer wall of the axial passage consisting of holes and, in order to provide a homogeneous heat distribution, said twin contacts including an axial, perimetric wall for providing a greater contact surface with the outer wall of the axial passage.

4. An electric heating device according to claim 3, wherein the twin contacts include respective extensions which extend radially over a length sufficient to project from a structure made up of the housing and the cover, in order to allow electric terminals of the heating element to be connected outside the housing.

5. An electric heating device according to claim 3, wherein the electric heating device is made up of five parts only consisting of the housing, the cover, the two twin electric contacts and the PTC element.

* * * * *